(12) United States Patent
Bhatt et al.

(10) Patent No.: US 11,760,730 B2
(45) Date of Patent: Sep. 19, 2023

(54) PROCESS FOR THE PREPARATION OF HIGH PURITY LEVOSIMENDAN

(71) Applicant: Navinta, LLC, Ewing, NJ (US)

(72) Inventors: Chiragkumar Anilkumar Bhatt, Vadodara (IN); Keyurkumar Amrutla Pandya, Vadodara (IN); Pankaj Vasudev Parmar, Vadodara (IN); John Muthiah Raja Jeyakumar, Vadodara (IN)

(73) Assignee: Navinta, LLC, Ewing, NJ (US)

( * ) Notice: Subject to any disclaimer, the term of this patent is extended or adjusted under 35 U.S.C. 154(b) by 0 days.

(21) Appl. No.: 17/572,331

(22) Filed: Jan. 10, 2022

(65) Prior Publication Data

US 2022/0220080 A1 Jul. 14, 2022

Related U.S. Application Data

(60) Provisional application No. 63/136,006, filed on Jan. 11, 2021.

(51) Int. Cl.
*C07D 237/14* (2006.01)

(52) U.S. Cl.
CPC .................. *C07D 237/14* (2013.01)

(58) Field of Classification Search
CPC .................................... C07D 237/14
See application file for complete search history.

(56) References Cited

U.S. PATENT DOCUMENTS

| | | | |
|---|---|---|---|
| 6,180,789 B1 | 1/2001 | Timmerbacka et al. | |
| 2004/0106617 A1 | 6/2004 | Backstrom et al. | |
| 2012/0165524 A1 | 6/2012 | Rao et al. | |

FOREIGN PATENT DOCUMENTS

| | | |
|---|---|---|
| EP | 0383449 A2 | 8/1990 |
| EP | 0565546 B1 | 3/1995 |
| EP | 0894087 B1 | 7/2005 |
| EP | 3424908 A1 | 1/2019 |

OTHER PUBLICATIONS

European Medicines Agency List of nationally authorised medicinal products Active substance levosimendan (Jun. 9, 2017), 4 pages.
International Search Report for Application No. PCT/US2022/011965 dated Mar. 30, 2022.

*Primary Examiner* — Rebecca L Anderson
(74) *Attorney, Agent, or Firm* — ST. ONGE STEWARD JOHNSTON & REENS LLC

(57) ABSTRACT

An improved process for the preparation of high purity Levosimendan includes treatment of Levosimendan crude with an organic acid, adding an organic acid to precipitate Levosimendan and isolating pure Levosimendan from the precipitate. Levosimendan obtained by the improved process is pharmaceutically acceptable with no impurity higher than 0.2 percent.

15 Claims, No Drawings

PROCESS FOR THE PREPARATION OF HIGH PURITY LEVOSIMENDAN

FIELD OF THE INVENTION

The present invention relates to an improved process for the preparation of high purity Levosimendan, wherein the process relates to purification of Levosimendan. In particular, the purification process of the present invention relates to obtaining high purity Levosimendan. The improved purification process of the present invention consists of treatment of crude Levosimendan with an organic acid.

BACKGROUND OF THE INVENTION

Levosimendan is an optically active (−) enantiomer of the racemic drug Simendan, chemically known as (−)-(R)[[4-(1,4,5,6-tetrahydro-4-methyl-6-oxo-3-pyridazinyl)phenyl]-hydrazono] propanedinitrile, which is represented by formula I.

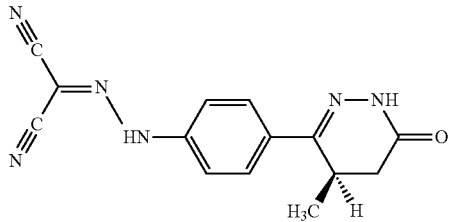

Formula I

Levosimendan belongs to a new class of drugs, calcium sensitizers, and is an active ingredient of the European drug SIMDAX®, which is intended for the short-term treatment of acutely decompensated severe chronic heart failure (ADHF) in situations where conventional therapy is not sufficient, and in cases where inotropic support is considered appropriate. SIMDAX® is not FDA approved.

Simendan was first described in EP0383449. Example 6 of said European patent application describes a process for the preparation of Simendan from 6-(4-aminophenyl)-5-methyl-4,5-dihydropyridazin-3(2H)-one intermediate by reacting with sodium nitrite and malononitrile in acidic conditions.

Levosimendan as an optically pure (−) enantiomer of Simendan was first described in EP0565546 and is reported to have better cardiotonic potency and solubility compared to racemic Simendan. According to EP0565546, Levosimendan can be obtained either by chiral phase chromatography of racemic Simendan or by converting the corresponding optically pure (−) enantiomer of 6-(4-aminophenyl)-5-methylpyridazin-3(2H)-one intermediate to Levosimendan as described in EP0383449, wherein the later one is preferred. The process according to EP0565546 comprises chiral resolution of 6-(4-aminophenyl)-5-methylpyridazin-3 (2H)-one intermediate using L-tartaric acid in 2-propanol and further crystallization using dioxane to obtain the desired enantiomer having 99.5% ee optical purity (Example 1), which is followed by converting (−)-6-(4-aminophenyl)-5-methylpyridazin-3(2H)-one to Levosimendan using sodium nitrite and malononitrile in acidic conditions, as described in EP0383449.

Another European patent application, EP0894087, describes conversion of (−)-6-(4-aminophenyl)-5-methylpyridazin-3(2H)-one to Levosimendan crude, which was further purified by refluxing the crude product in acetone/water to obtain pure Levosimendan. However, the heating at reflux temperature leads to degradation of Levosimendan and thus very high yield loss is observed, which makes this process commercially unfeasible. According to EP0894087, Levosimendan crude is subjected to reflux in acetone/water in the presence of activated carbon and hyflow, followed by hot filtration to yield 0.38 w/w of final Levosimendan. When the inventors repeated these experimental conditions, we found that the isolated Levosimendan contained an unknown impurity at more than 0.39% and the purity of Levosimendan was less than 99.5%. From mass analysis, it was determined that the molecular weight of the unknown impurity is about 561.55. The inventors have found that Levosimendan is prone to degradation at high temperature and this impurity is generated due to reflux temperature.

European application EP3424908 also describes conversion of (−)-6-(4-aminophenyl)-4,5-dihydro-5-methyl-3-(2H)-pyridazinone intermediate to Levosimendan crude followed by purification from ethanol and diethyl ether in order to obtain pure Levosimendan.

It can be summarized from these references that Levosimendan obtained from (−)-6-(4-aminophenyl)-5-methylpyridazin-3(2H)-one is crude in nature and requires additional purification step(s) to achieve pure Levosimendan having a purity required for its use as a pharmaceutical agent. The purification processes known in the art involve multiple treatments with high volumes of solvents and/or water at reflux temperature, which results in yield loss.

It is therefore an objective of the present invention to overcome the disadvantages of the prior processes and to develop an improved and scalable process to obtain high purity Levosimendan that is pharmaceutically acceptable.

SUMMARY OF THE INVENTION

We have found that treatment of Levosimendan crude with a solution of an organic acid removes the undesired impurities and provides highly pure Levosimendan.

In a first aspect, the present application discloses a process for purification of Levosimendan comprising the steps of:
dissolving Levosimendan crude in an organic solvent, water, or a mixture thereof;
adding an organic acid to the dissolved crude to precipitate Levosimendan; and
isolating pure Levosimendan from the precipitate.

In some embodiments, the organic solvent comprises a ketone, alcohol, or ester functional group. In some of those embodiments, the organic solvent is/consists of a ketone. Preferably, the organic solvent is acetone.

In certain embodiments, the dissolving step is carried out at ambient temperature.

In some embodiments, the organic acid is selected from carboxylic acids or derivatives thereof. In some of those embodiments, the carboxylic acids are selected from the group consisting of substituted or un-substituted Succinic acid, Fumaric acid, Citric acid, Tartaric acid, Mandelic acid, Oxalic acid, Acetic acid, Propionic acid, Acrylic acid, Lactic acid, Pyruvic acid, Butyric acid, Malic acid, Gluconic acid, and combinations thereof. In certain embodiments, the organic acid is dissolved in a solvent and added as a solution. In certain of those embodiments, the organic acid solution is added at a temperature between 0 and 5° C. until the pH of the reaction mixture is about 2 to about 4.

In certain embodiments, the process of purifying further comprises passing the dissolved Levosimendan crude through a filter.

In some embodiments, the isolating comprises precipitation by cooling followed by filtration of the precipitate.

In certain embodiments, the process of purifying further comprises washing the isolated Levosimendan with the organic solvent, water, or a mixture thereof.

In some embodiments, the process of purifying further comprises a step of washing with a weak base selected from inorganic weak bases or salts of organic acids, wherein the washing can occur after the adding step and/or after the isolating step. In some of those embodiments, the weak base is selected from the group consisting of sodium carbonate, potassium carbonate, sodium bicarbonate, potassium bicarbonate, sodium acetate, potassium acetate, ammonium acetate and basic salts of the organic acid.

In some embodiments, the process of purifying further comprises removing unbound solvent or water from the isolated Levosimendan.

In a second aspect, the present disclosure provides high purity Levosimendan, which is obtained by the purification process(es) described herein. The Levosimendan is advantageously pharmaceutically acceptable and no impurity is higher than 0.2. Moreover, Levosimendan prepared by the purification processes described herein is free of unknown impurity having molecular weight of about 561.55.

In a third aspect, the present disclosure provides a process for the preparation of high purity Levosimendan comprising the processes described herein for the purification of Levosimendan.

A process for the preparation of pharmaceutically acceptable Levosimendan comprises chirally resolving a racemic mixture of (±)-6-(4-aminophenyl)-5-methylpyridazin-3(2H)-one to yield (−)-6-(4-aminophenyl)-5-methylpyridazin-3(2H)-one;

converting the (−)-6-(4-aminophenyl)-5-methylpyridazin-3(2H)-one to Levosimendan crude;

dissolving the Levosimendan crude in organic solvent, water, or a mixture thereof;

adding an organic acid to the dissolved crude to precipitate Levosimendan; and isolating pure Levosimendan.

Preferably, the organic solvent is a ketone and the organic acid is selected from carboxylic acids or derivatives thereof.

In some embodiments, chirally resolving comprises generation of (−)-6-(4-aminophenyl)-5-methylpyridazin-3(2H)-one (Intermediate 1) salt with an optically active organic acidic. In certain of those embodiments, the Intermediate 1 salt is treated in-situ with a weak base, such as sodium carbonate, potassium carbonate, sodium bicarbonate or potassium bicarbonate to arrive at Intermediate 1. In other embodiments, Intermediate 1 is isolated with an optically active organic acid prior to treating it with a weak base. In preferred embodiments, an organic acid used in the step of chirally resolving is a D-isomer of tartaric acid, di-p-anisoyl-tartaric acid, di-p-tolyl-tartaric acid or O, O'-dibenzoyl-tartaric acid.

In some embodiments, converting (−)-6-(4-aminophenyl)-5-methylpyridazin-3(2H)-one to Levosimendan crude comprises reacting Intermediate 1 with sodium nitrite and malononitrile in acidic conditions.

In certain embodiments, dissolving Levosimendan crude comprises dissolving in an organic solvent. In some of those embodiments, the organic solvent is a ketone, alcohol, or ester. In some preferred embodiments, the solvent for dissolving Levosimendan crude is acetone. In some embodiments, dissolving Levosimendan crude is carried out at room temperature. In certain embodiments, dissolving Levosimendan crude further comprises passing the dissolved Levosimendan through a filter to remove any insoluble solids.

In some embodiments, a carboxylic acid or derivative thereof used in the adding step is selected from substituted or un-substituted Succinic acid, Fumaric acid, Citric acid, Tartaric acid, Mandelic acid, Oxalic acid, Acetic acid, Propionic acid, Acrylic acid, Lactic acid, Pyruvic acid, Butyric acid, Malic acid, Gluconic acid, and combinations thereof. In some embodiments, a salt of the organic acid is used. In certain of those embodiments, the salt is an alkali metal ion salt, preferably sodium or potassium salt of the corresponding organic acid. In certain embodiments, the organic acid of the adding step is dissolved in a solvent and added as a solution. In certain of those embodiments, the organic acid solution is added a temperature between 0 and 5° C. until the pH of the reaction mixture is about 2 to about 4.

In some embodiments, isolating comprises precipitation by cooling followed by filtration of the precipitate.

In certain embodiments, the process of preparing Levosimendan further comprises washing the isolated Levosimendan with the organic solvent, water, or a mixture thereof used in the dissolving step.

In some embodiments, the process of preparing Levosimendan further comprises a step of washing with a weak base selected from inorganic weak bases or salts of organic acids, wherein the washing can occur after the adding step and/or after the isolating step. In some of those embodiments, the weak base is selected from the group consisting of sodium carbonate, potassium carbonate, sodium bicarbonate, potassium bicarbonate, sodium acetate, potassium acetate, ammonium acetate and basic salts of the organic acid.

In certain embodiments, the process of preparing Levosimendan further comprises a step of removing unbound solvent or water from the isolated Levosimendan.

The processes for preparing Levosimendan described herein do not require reflux of Levosimendan crude and/or water at reflux temperatures.

Advantageously, Levosimendan prepared by the processes described is pharmaceutically acceptable and contains no impurity at higher than 0.2 percent by weight. Moreover, Levosimendan prepared by the processes described herein is free of unknown impurity having molecular weight of about 561.55.

DETAILED DESCRIPTION OF THE INVENTION

The invention will now be described in further detail.

Definitions

The term "organic acid" as used herein refers to organic compounds with acidic properties. For purposes of the present invention, the organic acid may be mono, di or tri carboxylic acids, of derivatives thereof, and combinations thereof. The carboxylic acids comprise but are not limited to substituted or un-substituted Succinic acid, Fumaric acid, Citric acid, Tartaric acid, Mandelic acid, Oxalic acid, Acetic acid, Propionic acid, Acrylic acid, Lactic acid, Pyruvic acid, Butyric acid, Malic acid, Gluconic acid. This list of organic acids is not exhaustive; it is intended to be illustrative and not limiting.

The term "pure" as used herein, refers to a substance that is suitable for use as drug for human consumption. The measure of whether a substance is pure is known as "purity".

The term "impurity" as used herein, refers to presence of undesired substance/molecule(s) in the pure substance. The term impurity includes "related substances", which refers to process related undesired substances, starting material related undesired substances, by-products and derivatives. If the substance contains chiral centers, the term "impurity" also includes "chiral impurity", which refers to undesired enantiomer(s) and/or diastereomer(s).

"Purity" and "impurity" of a sample are measured by various techniques, wherein purity by HPLC is a widely used method for pharmaceutical substances.

The term "Levosimendan crude" refers to Levosimendan having a purity that is lesser than acceptable pharmaceutical grade. The impurity as referred herein also includes undesired enantiomer or other impurities.

The term "pure Levosimendan" refers to Levosimendan having a purity that is equal to or greater than the acceptable pharmaceutical grade. The term may also refer to Levosimendan having no individual known or unknown impurities greater than 0.2%. Impurity as referred herein also includes undesired enantiomer or other impurities.

The term "pharmaceutically acceptable" as used herein refers to a product having purity greater than 99.5%.

The term "ambient temperature" means a temperature ranging from about 20° C. to 40° C., preferably to a temperature ranging from about 25° C. to 35° C.

The term "about" is to be construed as modifying a term or value such that it is not an absolute. Such terms will be defined by the circumstances. This includes, at the very least, the degree of expected experimental variability, technique variability and instrument variability for a given technique used to measure a value.

The term "comprising" and "comprises" mean the elements recited, or their equivalents in structure or function, plus any other element or elements which are not recited.

The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "racemic" means mixture of two more stereoisomers, which is commonly a mixture in about equal proportion.

The terms "chiral resolution/resolve" are intended to encompass the complete or partial separation of two optical enantiomers.

The term "resolving agent" means those optically active compounds used for "chiral resolution" of a racemic substance.

Abbreviations

HPLC High Performance Liquid Chromatography
SMUI Single Maximum Unknown Impurity
RRT Relative Retention Time
ND Not Detected In a first aspect, a process for the purification of Levosimendan comprises the steps of:
a. dissolving Levosimendan crude in organic solvent, water, or a mixture thereof;
b. adding an organic acid to the dissolved crude of step a; and
c. isolating pure Levosimendan.

The organic solvent of step a comprises a ketone, alcohol or ester functional group, preferably a solvent with a ketone functional group, more preferably, acetone. Step-a may be carried out at ambient temperature, and the dissolved crude is optionally passed through a filter to remove any insoluble solids.

The organic acid of step b is selected from carboxylic acids or derivatives thereof. The carboxylic acids comprise but are not limited to substituted or un-substituted Succinic acid, Fumaric acid, Citric acid, Tartaric acid, Mandelic acid, Oxalic acid, Acetic acid, Propionic acid, Acrylic acid, Lactic acid, Pyruvic acid, Butyric acid, Malic acid, Gluconic acid. The list of organic acids is intended to be illustrative and shall not be construed as exhaustive.

In step-b, the organic acid is added to the reaction mixture of step-a as solution, and the organic acid is dissolved in an organic solvent, water or a mixture thereof; the organic solvent may be the same as that used in step-a; preferably an aqueous solution of an organic acid is used.

The addition of a solution of an organic acid is optionally carried out at a lower temperature, preferably between 0-5° C., until the pH of the reaction mixture is about 2 to 4.

Step-c: pure Levosimendan may be isolated by methods known in the art, such as precipitation, crystallization, cooling, filtration, centrifugation or combination thereof. Preferably, pure Levosimendan is isolated by precipitation by cooling, followed by filtration. The isolated pure Levosimendan is optionally washed with organic solvent as used in step-a, water or a mixture thereof.

Optionally, Levosimendan is further subjected to washing with a weak base, wherein the weak base is selected from inorganic weak bases or salts of organic acids; preferably, the weak base is selected from sodium carbonate, potassium carbonate, sodium bicarbonate, potassium bicarbonate, sodium acetate, potassium acetate, ammonium acetate and/or basic salts of organic acids of step-b. Optionally, the reaction mixture of step-b may directly be subjected to washing using a weak base followed by isolation of pure Levosimendan in step-c.

The obtained pure Levosimendan is optionally dried by methods such as vacuum drying, heat drying, spray drying, freeze drying, supercritical drying or natural air drying. Any of the mentioned methods may also be used in combination to ensure removal of unbound solvent or water. As will be recognized, the drying time will depend upon, amongst other things, such as the amount of material to be dried, and particular drying method used.

Optionally, the obtained pure Levosimendan may further be subjected to additional processing steps to achieve desired physical property.

We have found that treatment of Levosimendan crude with an organic acid provides Levosimendan of high purity as compared to the earlier processes known in the art.

In one aspect, the improved process of the present invention comprises treatment of Levosimendan crude with an organic acid solution to isolate pure Levosimendan.

The improved purification process is capable of achieving high purity and is suitable for manufacturing at commercial scale.

In one embodiment, the present invention involves treatment of Levosimendan crude solution with an organic acid solution at ambient temperature or at a temperature below 10° C. to isolate Levosimendan having a purity greater than 99.5%.

The following table shows purity and impurities of Levosimendan prepared in accordance with the invention using various organic acids.

|  | HPLC purity | | |
| --- | --- | --- | --- |
| Process/Reference | Levosimendan | Imp at RRT 0.79 | Imp at RRT 1.58 |
| Prior-art processes and results | | | |
| EP0894087 B1 (Acetone/water at reflux) | Purity result is not disclosed | | |
| Repetition of EP0894087 B1 (Acetone/water at reflux) | 99.43% | 0.39% | 0.05% |
| Processes of present invention and results | | | |
| Leyosimendan Crude | 99.18% | 0.01% | 0.30% |
| Citric acid | 99.87% | 0.01% | 0.06% |
| Acetic acid | 99.93% | 0.02% | 0.05% |
| Tartaric acid | 99.88% | 0.01% | 0.06% |
| Mandelic acid | 99.88% | 0.02% | 0.05% |
| Oxalic acid | 99.89% | 0.02% | 0.05% |
| Succinic acid | 99.94% | ND | 0.06% |
| Fumaric acid | 99.88% | 0.02% | 0.06% |
| Acrylic acid | 99.84% | 0.01% | 0.1% |
| Lactic acid | 99.86% | 0.02% | 0.1% |
| Malic acid | 99.82% | 0.01% | 0.15% |
| Gluconic acid | 99.82% | ND | 0.15% |

From the above data, it is evident that treatment of Levosimendan crude with an organic acid according to the improved process of the present invention provides Levosimendan of high purity.

Treatment with an organic acid solution avoids reflux temperature, which possibly results in lower degradation and thus high purity.

The process results in yields that are advantageous to scalable process operations.

A process for the preparation of high purity Levosimendan comprises the process for the purification of Levosimendan as disclosed herein. That is, the process for the preparation of high purity Levosimendan comprises treatment of Levosimendan crude with an organic acid.

In particular, a process for the preparation of high purity Levosimendan comprises:

I. chiral resolution of racemic (±)-6-(4-aminophenyl)-5-methylpyridazin-3(2H)-one,
II. converting (−)-6-(4-aminophenyl)-5-methylpyridazin-3(2H)-one (Intermediate 1) to Levosimendan crude;
III. dissolving Levosimendan crude in organic solvent, water, or a mixture thereof;
IV. adding organic acid to the dissolved crude of Step III, and
V. isolating high purity Levosimendan.

Step I: chiral resolution can be carried out using optically active resolving agents known in the art, such as: tartaric acid, mandelic acid and derivatives thereof; preferably, the organic acid for resolution is a D-isomer of tartaric acid, di-p-anisoyl-tartaric acid, di-p-tolyl-tartaric acid or O,O'-dibenzoyl-tartaric acid. Step I comprises generation of a salt of (−)-6-(4-aminophenyl)-5-methylpyridazin-3(2H)-one (Intermediate 1) with optically active organic acidic resolving agent, which may be followed by in-situ treatment with a weak base, such as sodium carbonate, potassium carbonate, sodium bicarbonate or potassium bicarbonate, to obtain (−)-6-(4-aminophenyl)-5-methylpyridazin-3(2H)one (Intermediate 1). Optionally, the salt of (−)-6-(4-aminophenyl)-5-methylpyridazin-3(2H) one (Intermediate 1) with an optically active organic acidic resolving agent is isolated prior to its treatment with weak base.

Step II: the conversion of Intermediate 1 to Levosimendan crude is carried out by processes known in the art, preferably, by reacting Intermediate 1 with sodium nitrite and malononitrile under acidic conditions.

Step III: Levosimendan crude is dissolved in organic solvent, such as ketone, alcohol, or ester functional group; preferably, the organic solvent is a solvent with a ketone functional group, more preferably, acetone. Step III may be carried out at ambient temperature, and the dissolved Levosimendan is optionally passed through a filter to remove any insoluble solids.

Step IV: the organic acid is selected from carboxylic acids or derivatives thereof. The carboxylic acids comprise of but not limited to substituted or un-substituted Succinic acid, Fumaric acid, Citric acid, Tartaric acid, Mandelic acid, Oxalic acid, Acetic acid, Propionic acid, Acrylic acid, Lactic acid, Pyruvic acid, Butyric acid, Malic acid, Gluconic acid. A salt of an organic acid can also be used. The list of organic acids is intended to be illustrative and not be construed exhaustive. In step IV, the organic acid is added to the reaction mixture of step III, wherein the organic acid is dissolved in organic solvent, water, or a mixture thereof and organic solvent is same as that used in step III preferably an aqueous solution of an organic acid is used.

The addition of solution of an organic acid may be carried out at lower temperature; preferably, between 0-5° C. until the pH of the reaction mixture is about 2 to 4.

Step V: Levosimendan may be isolated by methods known in the art, such as precipitation, crystallization, cooling, filtration, centrifugation, or combinations thereof; preferably, pure Levosimendan is isolated by precipitation by cooling followed by filtration. In step V, the isolated Levosimendan may optionally be washed with water.

Optionally, Levosimendan is further subjected to washing with a weak base, wherein the weak base is selected from inorganic weak bases or basic salt of organic acids; preferably, the weak base is selected from sodium carbonate, potassium carbonate, sodium bicarbonate, potassium bicarbonate, sodium acetate, ammonium acetate or basic salt of organic acids of step-d. Optionally, the reaction mixture of step IV may be directly subjected to in-situ washing with a weak base followed by isolation of pure Levosimendan in step V.

Thus obtained pure Levosimendan is optionally dried by methods such as vacuum drying, heat drying, spray drying, freeze drying, supercritical drying or natural air drying. Any of the mentioned methods may also be used in combination to ensure removal of unbound solvent or water. As will be recognized, the drying time will depend upon, amongst other things, the amount of material to be dried, and the particular drying method used. Optionally, the obtained pure Levosimendan may further be subjected to additional processing steps to achieve desired physical properties.

High purity Levosimendan is produced having any single maximum unknown impurity which is 0.2% or less as measured by HPLC.

The Levosimendan crude used as a starting material in the purification of the present invention may be prepared according to the methods known in art or as depicted in the scheme below:

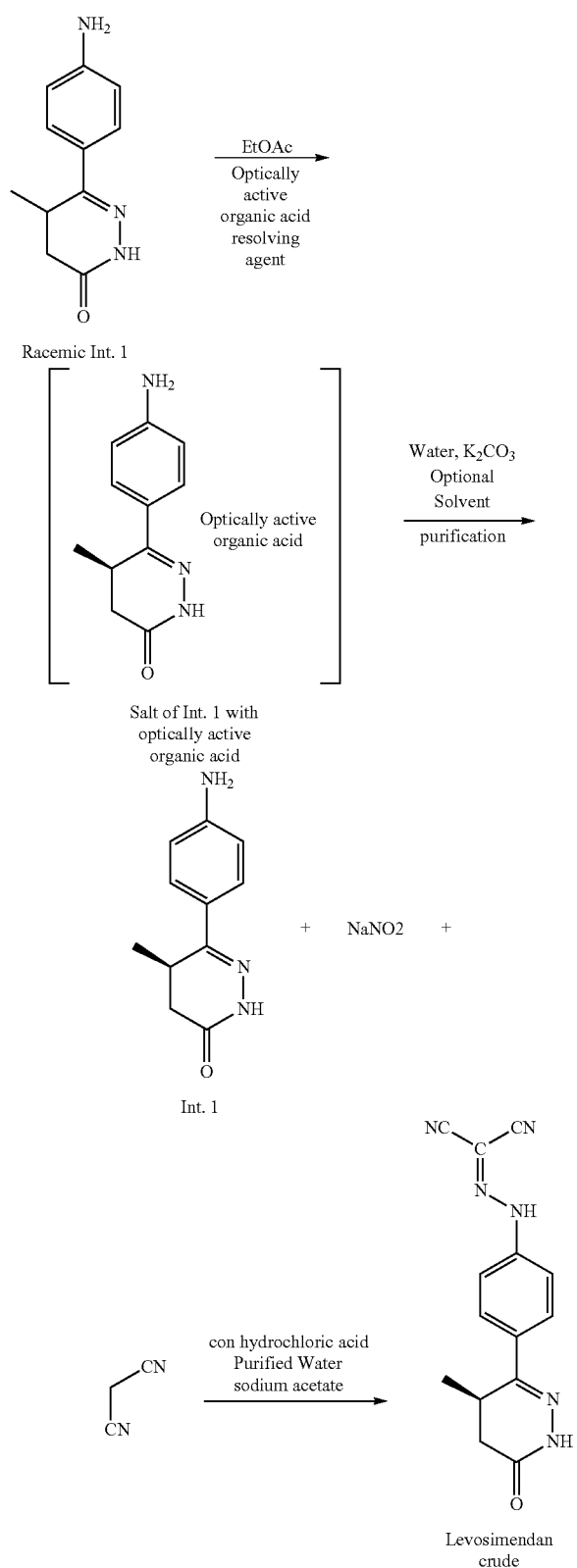

Chiral resolution of Racemic (±)-6-(4-aminophenyl)-5-methylpyridazin-3(2H)-one in at least one optically active organic acidic resolving agent known in the art and as described in the second aspect of the present invention to obtain (−)-6-(4-aminophenyl)-5-methylpyridazin-3(2H)-one (Intermediate 1) salt with optically active organic acidic resolving agents is followed by neutralization of the salt with potassium carbonate to yield (−)-6-(4-aminophenyl)-5-methylpyridazin-3(2H)-one (Intermediate 1). Further reaction of (−)-6-(4-aminophenyl)-5-methylpyridazin-3(2H)-one (Intermediate1) with sodium nitrite and malononitrile in acidic conditions yields Levosimendan crude.

EXAMPLES

Detailed experimental procedures to illustrate the improved process for the purification of Levosimendan or a salt thereof according to the present invention are provided by the following examples, which are intended to be illustrative and not limiting. The purification processes produce pharmaceutically acceptable Levosimendan.

Reference Example 1: Chiral Resolution of Racemic (±)-6-(4-aminophenyl)-5-methylpyridazin-3(2H)-one 100 g of racemic (±)-6-(4-aminophenyl)-5-methylpyridazin-3(2H)-one (Racemic Intermediate 1) was added to ethyl acetate (3000 mL) and water (95 mL) mixture at ambient temperature. The solution was charged with D (−)-Tartaric acid (75.32 g) and stirred for about 90 minutes at ambient temperature. The reaction mixture was seeded with D-tartrate salt of Intermediate 1 and stirred for 90-100 minutes at ambient temperature followed by heating at 56.0° C.±2.0° C. and stirred for further 120-130 minutes maintaining the same temperature. The hot reaction mixture was filtered and the solid D-tartrate Salt of Intermediate 1 was washed with hot ethyl acetate (100 mL). Wet D-tartrate salt of Intermediate 1 was suspended in water and basified to pH 9.0 to 10.0 using potassium carbonate solution at below 10° C. The solid Intermediate 1 was filtered and wet cake was washed with water (450 mL). Thus obtained (−)-6-(4-aminophenyl)-5-methylpyridazin-3(2H)-one (crude Intermediate 1) is dried under vacuum at 50° C.±5.0° C. for 8 hours. The dried (−)-6-(4-aminophenyl)-5-methylpyridazin-3(2H)-one (crude Intermediate 1) (40 g) is charged with 1, 4-Dioxane (480 mL) and stirred at 98.5° C.±2.5° C. until a clear solution is obtained. The reaction mixture is cooled at 14.0° C.±2.0° C. and further stirred for 55 to 65 minutes. The solid (racemic mixture of Intermediate 1) was filtered. The filtrate was heated at 37.5° C.±2.5° C. and charged activated charcoal (4 g) followed by filtration through a hyflow supercell bed. The bed was washed with 1,4-dioxane (20 mL) and the combined filtrate was distilled under vacuum at 52.5° C.±2.5° C. The residue was charged with isopropanol (20 mL) at 52.5° C.±2.5° C., stirred for 10-15 minutes followed by distillation of solvent. The residues were again charged with isopropanol (20 mL) at 52.5° C.±2.5° C., stirred for 10-15 minutes and distilled. The residues were added to isopropanol (80 mL) at 52.5° C.±2.5° C. and stirred for 10-15 minutes. The reaction mixture was cooled at 27.5° C.±2.5° C. and further stirred for about 30 minutes. The solid was filtered, washed with isopropanol (60 mL) and dried under vacuum at 50° C.±2.0° C. for 8 hours to get 26.0 g of the desired (−)-6-(4-aminophenyl)-5-methylpyridazin-3(2H)-one (Intermediate 1).

HPLC Purity: 99.80%, Chiral Purity: more than 99.5%

Reference Example 2: Preparation of Levosimendan Crude 100 g of (−)-6-(4-aminophenyl)-5-methylpyridazin-3(2H)-one (Intermediate1) was added to an aqueous hydrochloric acid solution (prepared by adding 200 mL conc. HCl in 1500 mL water), cooled and followed by slow addition of an aqueous solution of sodium nitrite (40 g in 400 mL water) at 0-5° C. and stirred for 30 minutes. An aqueous solution of Malononitrile (32.5 g in 400 mL water) is slowly added to the above reaction mass while maintaining the temperature at 0-5° C. till the reaction was complete. The reaction mass was adjusted to pH 5.0±0.2 by addition of an aqueous solution of sodium acetate (prepared by dissolving 1200 g in 3000 mL water) and the precipitated solid was filtered followed by slurry wash (3000 mL water) to get 300 g wet Levosimendan crude. The wet material was used as-is for following examples 1 to 7 of the present invention.

HPLC Purity: 99.18%, SMUI: 0.3%

Example 1: Process for the Purification of Levosimendan Crude by Citric Acid Treatment Wet solid of Levosimendan crude (300 g, from Reference Example 2) was dissolved in acetone (2300 mL) and water (390 mL) and stirred for 40 minutes at 25-30° C. Solution was filtered to remove any insoluble solids and the filtrate was cooled at 0-5° C. An aqueous solution of citric acid (prepared by dissolving 80 g of citric acid in 100 mL water) was added to this filtrate and allowed to stir for 3.5 hours at 0-5° C. The solid formed was filtered and washed with acetone. The wet solid was charged in water (1000 mL) followed by pH adjustment of the supernatant by addition of aqueous solution of sodium acetate (35 g in 100 mL water) to pH=5.5, the resulting reaction mass was allowed to stir for 90 minutes at 0-5° C. The resulting solid was filtered, and slurry washed with water followed by drying under vacuum at 40-45° C. to get 88.0 g Levosimendan.

HPLC Purity: 99.87%, SMUI: 0.06%

Example 2: Process for the Purification of Levosimendan Crude by Acetic Acid Treatment Wet solid of Levosimendan crude (7.76 g derived from 2 g of Intermediate 1) was dissolved in acetone (46 mL) and water (6 mL) and stirred for 40 minutes at 25-30° C. Solution was filtered to remove any insoluble solid particles and the filtrate was cooled at 0-5° C. An aqueous solution of acetic acid (0.5 g in 2 mL water) was added to the solution of Levosimendan crude in acetone/water and allowed to stir for 3.5 hours at 0-5° C. The solid was filtered and washed with acetone. The wet solid was charged in water (10 mL) followed by pH adjustment by addition of aqueous solution of sodium acetate (prepared by dissolving 0.7 g in 2 mL water) to pH=5.5, the resulting reaction mass was allowed to stir for 90 minutes at 0-5° C. The resulting solid was filtered and slurry washed with water followed by drying under vacuum at 40-45° C. to get 1.44 g Levosimendan. HPLC Purity: 99.93%, SMUI: 0.05%

HPLC Purity: 99.93%, SMUI: 0.05%

Example 3: Process for the Purification of Levosimendan Crude by Tartaric Acid Treatment Wet solid of Levosimendan crude (7.76 g derived from 2 g of Intermediate 1) was dissolved in acetone (46 mL) and water (6 mL) and stirred for 40 minutes at 25-30° C. Solution was filtered to remove any insoluble solid particles and the filtrate was cooled at 0-5° C. An aqueous solution of tartaric acid (prepared by dissolving 1.23 g in 2 mL water) was added to the solution of Levosimendan crude in acetone/water and allowed to stir for 3.5 hours at 0-5° C. The solid was filtered and washed with acetone. The wet solid was charged in water (10 mL) followed by pH adjustment by addition of aqueous solution of sodium acetate (0.7 g in 2 mL water) to pH=5.5, the resulting reaction mass was allowed to stir for 90 minutes at 0-5° C. The resulting solid was filtered and slurry washed with water followed by drying under vacuum at 40-45° C. to get 1.74 g Levosimendan.

HPLC Purity: 99.88%, SMUI: 0.06%

Example 4: Process for the Purification of Levosimendan Crude by Mandelic Acid Treatment Wet solid of Levosimendan crude (7.76 g derived from 2 g of Intermediate 1) was dissolved in acetone (46 mL) and water (6 mL) and stirred for 40 minutes at 25-30° C. Solution was filtered to remove any insoluble solid particles and the filtrate was cooled at 0-5° C. An aqueous solution of mandelic acid (prepared by dissolving 1.24 g in 2 mL water) was added to the solution of Levosimendan crude in acetone/water and allowed to stir for 3.5 hours at 0-5° C. The solid was filtered and washed with acetone. The wet solid was charged in water (10 mL) followed by pH adjustment by addition of aqueous solution of sodium acetate (0.7 g in 2 mL water) to pH=5.5, the resulting reaction mass was allowed to stir for 90 minutes at 0-5° C. The resulting solid was filtered and slurry washed with water followed by drying under vacuum at 40-45° C. to get 1.77 g Levosimendan.

HPLC Purity: 99.88%, SMUI: 0.05%

Example 5: Process for the Purification of Levosimendan Crude by Oxalic Acid Treatment Wet solid of Levosimendan crude (7.76 g derived from 2 g of Intermediate 1) was dissolved in acetone (46 mL) and water (6 mL) and stirred for 40 minutes at 25-30° C. Solution was filtered to remove any insoluble solid particles and the filtrate was cooled at 0-5° C. An aqueous solution of oxalic acid (prepared by dissolving 0.73 g in 2 mL water) was added to the solution of Levosimendan crude in acetone/water and allowed to stir for 3.5 hours at 0-5° C. The solid was filtered and washed with acetone. The wet solid was charged in water (10 mL) followed by pH adjustment by addition of aqueous solution of sodium acetate (0.7 g in 100 mL water) to pH=5.5, the resulting reaction mass was allowed to stir for 90 minutes at 0-5° C. The resulting solid was filtered and slurry washed with water followed by drying under vacuum at 40-45° C. to get 1.43 g Levosimendan.

HPLC Purity: 99.89%, SMUI: 0.05%

Example 6: Process for the Purification of Levosimendan Crude by Succinic Acid Treatment Wet solid of Levosimendan crude (7.76 g derived from 2 g of Intermediate 1) was dissolved in acetone (46 mL) and water (6 mL) and stirred for 40 minutes at 25-30° C. Solution was filtered to remove any insoluble solid particles and the filtrate was cooled at 0-5° C. An aqueous solution of succinic acid (prepared by dissolving 0.73 g in 2 mL water) was added to the solution of Levosimendan crude in acetone/water and allowed to stir for 3.5 hours at 0-5° C. The solid was filtered and washed with acetone. The wet solid was charged in water (10 mL) followed by pH adjustment by addition of aqueous solution of sodium acetate (0.7 g in 100 mL water) to pH=5.5, the resulting reaction mass was allowed to stir for 90 minutes at 0-5° C. The resulting solid was filtered and slurry washed with water followed by drying under vacuum at 40-45° C. to get 1.65 g Levosimendan.

HPLC Purity: 99.94%, SMUI: 0.06

Example 7: Process for the Purification of Levosimendan Crude by Fumaric Acid Treatment Wet solid of Levosimendan crude (7.76 g derived from 2 g of Intermediate 1) was dissolved in acetone (46 mL) and water (6 mL) and stirred for 40 minutes at 25-30° C. Solution was filtered to remove any insoluble solid particles and the filtrate was cooled at 0-5° C. An aqueous solution of fumaric acid (prepared by dissolving 0.73 g in 2 mL water) was added to the solution of Levosimendan crude in acetone/water and allowed to stir for 3.5 hours at 0-5° C. The solid was filtered and washed with acetone. The wet solid was charged in water (10 mL) followed by pH adjustment by addition of aqueous solution of sodium acetate (0.7 g in 100 mL water) to pH=5.5, the resulting reaction mass was allowed to stir for 90 minutes at 0-5° C. The resulting solid was filtered and slurry washed with water followed by drying under vacuum at 40-45° C. to get 1.69 g Levosimendan.

HPLC Purity: 99.88%, SMUI: 0.06%.

Example 8: Process for the Purification of Levosimendan Crude by Acrylic Acid Treatment Wet solid of Levosimendan crude (7.26 g derived from 2 g of Intermediate 1) was dissolved in acetone (46 mL) and water (6.5 mL) and stirred for 40 minutes at 25-30° C. Solution was filtered to remove any insoluble solid particles and the filtrate was cooled at 0-5° C. An aqueous solution of acrylic acid (prepared by dissolving 0.6 g in 2 mL water) was added to the solution of Levosimendan crude in acetone/water and allowed to stir for 3.5 hours at 0-5° C. The solid was filtered and washed with acetone. The wet solid was charged in water (20 mL) followed by pH adjustment by addition of aqueous solution of sodium acetate (0.7 g in 100 mL water) to pH=6.7, the resulting reaction mass was allowed to stir for 90 minutes at 0-5° C. The resulting solid was filtered and slurry washed with water followed by drying under vacuum at 40-45° C. to get 1.51 g Levosimendan.

HPLC Purity: 99.84%, SMUI: 0.1%.

Example 9: Process for the Purification of Levosimendan Crude by Lactic Acid Treatment Wet solid of Levosimendan crude (7.26 g derived from 2 g of Intermediate 1) was dissolved in acetone (46 mL) and water (6.5 mL) and stirred for 40 minutes at 25-30° C. Solution was filtered to remove any insoluble solid particles and the filtrate was cooled at 0-5° C. An aqueous solution of lactic acid (prepared by dissolving 0.81 mL in 2 mL water) was added to the solution of Levosimendan crude in acetone/water and allowed to stir for 3.5 hours at 0-5° C. The solid was filtered and washed with acetone. The wet solid was charged in water (20 mL) followed by pH adjustment by addition of aqueous solution of sodium acetate (0.7 g in 100 mL water) to pH=5.8, the resulting reaction mass was allowed to stir for 90 minutes at 0-5° C. The resulting solid was filtered and slurry washed with water followed by drying under vacuum at 40-45° C. to get 1.68 g Levosimendan.

HPLC Purity: 99.86%, SMUI: 0.1%.

Example 10: Process for the Purification of Levosimendan Crude by Malic Acid Treatment Wet solid of Levosimendan crude (7.26 g derived from 2 g of Intermediate 1) was dissolved in acetone (46 mL) and water (6.5 mL) and stirred for 40 minutes at 25-30° C. Solution was filtered to remove any insoluble solid particles and the filtrate was cooled at 0-5° C. An aqueous solution of malic acid (prepared by dissolving 1.1 g in 2 mL water) was added to the solution of Levosimendan crude in acetone/water and allowed to stir for 3.5 hours at 0-5° C. The solid was filtered and washed with acetone. The wet solid was charged in water (20 mL) followed by pH adjustment by addition of aqueous solution of sodium acetate (0.7 g in 100 mL water) to pH=5.8, the resulting reaction mass was allowed to stir for 90 minutes at 0-5° C. The resulting solid was filtered and slurry washed with water followed by drying under vacuum at 40-45° C. to get 1.68 g Levosimendan.

HPLC Purity: 99.82%, SMUI: 0.15%.

Example 11: Process for the Purification of Levosimendan Crude by Gluconic Acid Treatment Wet solid of Levosimendan crude (7.26 g derived from 2 g of Intermediate 1) was dissolved in acetone (46 mL) and water (6.5 mL) and stirred for 40 minutes at 25-30° C. Solution was filtered to remove any insoluble solid particles and the filtrate was cooled at 0-5° C. An aqueous solution of gluconic acid (prepared by dissolving 3.13 g in 2 mL water) was added to the solution of Levosimendan crude in acetone/water and allowed to stir for 3.5 hours at 0-5° C. The solid was filtered and washed with acetone. The wet solid was charged in water (20 mL) followed by pH adjustment by addition of aqueous solution of sodium acetate (0.7 g in 100 mL water) to pH=5.8, the resulting reaction mass was allowed to stir for 90 minutes at 0-5° C. The resulting solid was filtered and slurry washed with water followed by drying under vacuum at 40-45° C. to get 1.68 g Levosimendan.

HPLC Purity: 99.82%, SMUI: 0.15%.

It is envisioned that pharmaceutical formulations and preparations of the present invention can be prepared by mixing the Levosimendan described herein with one or more pharmaceutically acceptable excipients and administered to patients in need thereof, such as those with heart failure or amyotrophic lateral sclerosis (ALS). Suitable excipients include, without limitation, povidone, citric acid and ethanol, and equivalents thereof.

The Levosimendan can be formulated as a solution, suspension, tablet or capsule. It is envisioned that, in one embodiment, the Levosimendan described herein can be formulated as a solution for injection at a concentration of about 2.5 mg/mL.

Doses administered can range from about 1 mg to about 25 mg of Levosimendan, or about 0.1 to 12 mg/kg.

It should be noted that the invention in its broader aspects is not limited to the specific details, representative compositions, methods, and processes, and illustrative examples described in connection with the preferred embodiments and preferred methods. Modifications and equivalents will be apparent to practitioners skilled in this art and are encompassed within the spirit and scope of the appended claims.

What is claimed is:

1. A process for the preparation of pharmaceutically acceptable Levosimendan comprising:
   chirally resolving a racemic mixture of (±)-6-(4-aminophenyl)-5-methylpyridazin-3(2H)-one to yield (−)-6-(4-aminophenyl)-5-methylpyridazin-3(2H)-one;
   converting the (−)-6-(4-aminophenyl)-5-methylpyridazin-3(2H)-one to Levosimendan crude;
   dissolving the Levosimendan crude in organic solvent, water, or a mixture thereof;
   adding an organic acid to the dissolved crude to precipitate Levosimendan; and
   isolating pure Levosimendan.

2. The process of claim 1, wherein the organic solvent is a ketone.

3. The process of claim 1, wherein the organic acid is selected from carboxylic acids.

4. The process of claim 1, wherein the organic solvent contains a ketone, alcohol, or ester functional group.

5. The process of claim 1, wherein the organic solvent is acetone.

6. The process of claim 1, wherein the dissolving step is carried out at ambient temperature.

7. The process of claim 1, further comprising passing the dissolved Levosimendan crude through a filter.

8. The process of claim 3, wherein the carboxylic acids are selected from the group consisting of substituted or un-substituted Succinic acid, Fumaric acid, Citric acid, Tartaric acid, Mandelic acid, Oxalic acid, Acetic acid, Propionic acid, Acrylic acid, Lactic acid, Pyruvic acid, Butyric acid, Malic acid, Gluconic acid, and combinations thereof.

9. The process of claim 1, wherein the organic acid is dissolved in a solvent and added as a solution.

10. The process of claim 9, wherein the organic acid solution is added at a temperature between 0 and 5° C. until the pH of the reaction mixture is between about 2 to about 4.

11. The process of claim 1, wherein the isolating comprises precipitation by cooling followed by filtration of the precipitate.

12. The process of claim 1, further comprising washing the isolated Levosimendan with the organic solvent, water, or a mixture thereof.

13. The process of claim 1, further comprising a step of washing with a weak base selected from inorganic weak bases or salts of organic acids, wherein the washing can occur after the adding step and/or after the isolating step.

14. The process of claim 13, wherein the weak base is selected from the group consisting of sodium carbonate, potassium carbonate, sodium bicarbonate, potassium bicarbonate, sodium acetate, potassium acetate, ammonium acetate and basic salts of the organic acid.

15. The process of claim 1, further comprising removing unbound solvent or water from the isolated Levosimendan.

* * * * *